United States Patent [19]
Pober et al.

[11] Patent Number: 5,602,305
[45] Date of Patent: Feb. 11, 1997

[54] IMMUNODEFICIENT ANIMAL MODEL FOR STUDYING T CELL-MEDIATED IMMUNE

[75] Inventors: Jordan S. Pober, Guilford; Christopher C. W. Hughes, New Haven; Allan G. Murray, Branford; Philip W. Askenase, Hamden, all of Conn.; Peter Petzelbauer, Vienna, Austria

[73] Assignee: Yale University, New Haven, Conn.

[21] Appl. No.: 220,900

[22] Filed: Mar. 31, 1994

[51] Int. Cl.⁶ .......................... C02N 15/00; A61K 49/00
[52] U.S. Cl. .......................... 800/2; 424/9.2; 424/93.71; 800/DIG. 5
[58] Field of Search .................................. 800/2; 424/9

[56] References Cited

PUBLICATIONS

Kawanura et al. Transplantation 53:659, 1992.
Rendt et al. J. of Immunl 151(12): 7324, 1993.
Carlsson et al J. of Immunol 146(4): 1065, 1992.
Yon et al J. Clin. Invest 91: 986, 1993.
Bay et al. J. Exp. Med 173:167, 1991.
Dvorak, H., et al., J. Exp. Med., 150, 322–337, (1979).
Dvorak, H., et al., Jrnl. of Investigative Dermatology, 74, 280–284, (1980).
Leszczynski, D., et al., Kidney Int'l., 31, 1311–1316, (1987).
Bishop, G. A., et al., Transplantation, 48, 408–414, (1989).
Matsumoto, Y. et al., Transplantation, 56, 69–75, (1993).
Rosenberg, A., et al., Annu. Rev. Immunol. 10, 333–58, (1992).
Mosier, D. E., et al., Nature, 335, 256–259, (1988).
Dorshkind, K., et al., Jrnl. of Immunol., 132, 1804–1808, (1984).
Schuler, W., et al., Cell, 46, 963–972, (1986).
Fulop, G. M., et al., Nature, 347, 479–482, (1990).
Carlsson, R., et al., Jrnl. of Immunol., 148, 1065–1071, (1992).
Duchosal, M. A., et al., Nature, 355, 258–262, (1992).
Leader, K. A., et al., Immunology, 76, 229–234, (1992).
Markham, R. B., et al., Infection and Immunity, 60, 2305–2308, (1992).
Cavacini, L. A., et al., Clin. exp. Immunol., 90, 135–140, (1992).
Furukawa, T., et al., Jpn. J. Cancer Res., 83, 894–898, (1992).
Hesselton, R. M., et al., Jrnl. Infectious Diseases, 168, 630–40, (1993).
Nonoyama, S., et al., Jrnl. of Immunol., 151, 3894–3901, (1993).
London, N. J. M., et al., Transplantation Proceedings, 23, p. 749, (1991).
Kawamura, T., et al., Transplantation, 53, 659–665, (1992).
Murphy, W. J., et al., Jrnl. of Immunol., 150, 3634–3642, (1993).
Rendt, K. E., et al., Jrnl of Immunol., 151, 7324–7336, (1993).
Tary–Lehmann, M., et al., J. Exp. Med., 175, 503–516, (1992).
Pober, J. S., et al., Jrnl. of Immunol., 136, 1680–1687, (1986).
Macy, E., et al., FASEB Jrnl., 2, 3003–3009, (1988).
Petzelbauer, P., et al., Jrnl. of Immunol., 151, 5062–5072, (1993).
Yan, Horng–Chin, et al., J. Clin. Invest., 91, 986–996, (1993).
Murphy, W. J., et al., Eur. J. Immunol. 22, 1421–1427, (1992).
Picker, L. J., et al., Nature, 349, 796–799, (1991).

*Primary Examiner*—Suzanne E. Ziska
*Attorney, Agent, or Firm*—Darby & Darby

[57] ABSTRACT

The present invention describes a novel immunodeficient rodent model comprising an organ graft, such as a human skin graft, said graft containing microvessels lined by endothelial cells, human T lymphocytes and, optionally, at least one agent capable of substantially depleting the rodent's Natural Killer cells. The human T lymphocytes are engrafted and circulating in the animal's blood, enabling interaction with the endothelial cells which can be allogenic to the donor for the skin graft. The immunodeficient rodent used can be a SCID mouse. Preferably, the endothelial cells are provided by grafting said human skin with an intact dermal superficial vascular plexus. This immunodeficient rodent can be used as a model for studying inflammatory human immune responses of the engrafted T lymphocytes to foreign antigen as well as for studying human allograft rejection, e.g. human microvessel destruction and the T cell-endothelial cell in vivo interactions associated with a human allograft rejection.

34 Claims, 2 Drawing Sheets

IMMUNODEFICIENT ANIMAL MODEL FOR STUDYING T CELL-MEDIATED IMMUNE

FIELD OF THE INVENTION

The present invention relates to a novel immunodeficient animal model for studying human T cell mediated immune responses. The model of this invention is useful in studying an inflammatory human immune response such as an allograft rejection of a donor organ or for studying an inflammatory immune response in reaction to other types of foreign agents, e.g. an antigen or microorganism.

BACKGROUND OF THE INVENTION

In this invention, an immunodeficient rodent is modified in order that when it receives a donor organ, or portion thereof, or a foreign agent, such as an antigen, the modified rodent mounts a T cell mediated response to the foreign organ or agent in a manner which permits its use as a model for human immune response to the organ or agent. One of the key aspects of this invention is that the rodent receives an organ graft combining microvessels lined with human endothelial cells as opposed to human T cells alone, enabling the rodent to mount a T cell mediated response which corresponds to the interaction of human T cells and human endothelial cells. In many cases, primates have been required to study such T cell mediated responses. Because of costs and difficulties associated with primate models, the various embodiments of this invention should enable significant advancement in understanding human immune responses and developing therapeutics relating thereto.

As background, it is noted that microvascular endothelial cells (EC) are thought to be the primary targets of acute allogeneic rejection reactions in vascularized allografts (1–5: numbers in parenthesis appear throughout the specification and correspond to publications listed numerically at the end of the description provided herein). Experiments in mice have shown that such reactions are mediated by alloantigen-specific T cells (reviewed in (6)). Consequently, many new therapeutic strategies are based on the concept of disrupting interactions between host T cells and graft EC. However, many of the molecules that mediate such interactions are sufficiently different between humans and rodents that it has been necessary to use primates even for the initial screening of inhibitory reagents. An in vivo model of human T cell-EC interactions would greatly advance the development of such reagents.

The human peripheral blood lymphocyte—severe combined immunodeficient (hu-PBL-SCID) mouse was previously introduced as a small animal model for studying the human immune system in vivo (7). C.B-17 mice homozygous for the severe combined immunodeficiency (SCID) mutation are extremely inefficient at re-arranging T and B cell antigen receptor genes (8–10)and although NK cell function is intact, these T and B cell-deficient animals are unable to mediate rejection of human xenogeneic grafts. Upon introduction of human peripheral blood lymphocytes such mice can respond to antigen by synthesizing human antibodies (7, 11–18). However, very few human T lymphocytes appear to circulate in the peripheral blood of hu-PBL-SCID mice, and there is little evidence T cell-mediated inflammatory reactions can develop in these animals (19–22). Indeed some investigators have found that human T cells become anergic in the SCID mouse microenvironment and are incapable of mediating inflammation (23).

The present invention was developed based on the belief that a major part of the difficulty in reconstituting T cell inflammatory function in the hu-PBL-SCID mouse may arise because murine EC lack critical human cell surface proteins necessary for appropriate recruitment and activation of human T lymphocytes. To explore this hypothesis, human skin with an intact dermal microvascular plexus was grafted onto a SCID mouse prior to reconstituting the mouse with human peripheral blood mononuclear leukocytes allogeneic to the skin donor. As a result it was discovered that the non-primate animal model of this invention is useful for studying human allograft rejection of donor skin as well as a model for studying immune responses in reaction to other types of foreign agents. The model generates a reproducible, stereotypic reaction in which human T cells infiltrate and destroy the human dermal microvessels.

In the present invention, the novel animal model and method of its preparation introduce several improvements over other known models. The animal model of the present invention (a) leads to perfusion of skin graft microvessels lined by human endothelial cells, and (b) produces sustained circulating levels of human T lymphocytes. In preferred embodiments, the organ graft is a split thickness adult skin specimen, rather than neonatal foreskin, for greater retention of the human microvessels (27). In addition, pretreatment of the animal model with a NK cell depletion agent in conjunction with a human lymphocyte inoculum leads to higher levels of circulating human T lymphocytes.

Although Kawamura et al have previously described "chronic" skin rejection in a SCID mouse model (20), they did not observe acute inflammation at the graft site. They only observed gradual fibrosis and some lymphocyte infiltrates, only if presensitized donors were used. Thus, their model is not appropriate for studying acute graft rejection. The animal model of the present invention differs from that of Kawamura et al in several respects. The present model demonstrates greater than 90% of the skin grafts are infiltrated by unsensitized allogeneic human T cells within a week of PBMC (peripheral blood mononuclear leukocytes) reconstitution. Secondly the observed destruction of human vascular elements within the skin is consistent with the time course seen in first set skin rejection in man (1). Thirdly, results obtained using the animal model of the present invention for allograft skin rejection suggest that the infiltrating T cells are activated in response to alloantigen. Differences in the modifications to the two models and methods employing them likely account for these discrepancies.

SUMMARY OF THE INVENTION

This invention relates to an immunodeficient rodent wherein the immunodeficient rodent comprises:

(i) an organ graft from a mammal, said graft containing microvessels lined by endothelial cells;

(ii) an effective amount of human T lymphocytes; and (iii) optionally, at least one agent capable of rendering inactive the Natural Killer cells of the rodent; said agent being present in an amount sufficient to substantially deplete the rodent's active Natural Killer cells. The depletion of the Natural Killer cells improves engraftment of human T lymphocytes.

The rodent model of this invention can be used to study human allograft rejection of a donor organ. Alternatively, the model can be used to conduct a study of an autologous human immune response to antigenic material other than organ, such as viral antigens.

Additional embodiments of the invention relate to methods of preparing the novel model as well as to the use of the model for identifying potential therapeutics for use in combatting undesirable immune responses, such as rejection of allografts and/or alleviating side-effects associated with allografts.

BRIEF DESCRIPTION OF THE DRAWINGS

Data represents the mean +/−SD of six mice.

DETAILED DESCRIPTION OF THE INVENTION

This invention relates to an immunodeficient rodent wherein the immunodeficient rodent comprises: (i) an organ graft from a mammal, said graft containing endothelial cells; (ii) an effective amount of human T lymphocytes; and (iii) optionally, at least one agent capable of rendering inactive the Natural Killer cells of the rodent; said agent being present in an amount sufficient to substantially deplete the rodent's active Natural Killer cells.

Alternative embodiments relate to the use of the model to study human allograft rejection of human skin. In such a case the model is directed to an immunodeficient rodent comprising: (i) a human skin graft, said graft containing endothelial cells; (ii) an effective amount of human T lymphocytes allogeneic to the donor for the skin graft; and (iii) optionally, at least one agent capable of rendering inactive the Natural Killer cells of the rodent; said agent being present in an amount sufficient to substantially deplete the rodent's active Natural Killer cells.

Although the invention may be applied to non-primate animals other rodents, such as a rabbit, rats or mice are preferred. Certainly mice are currently the most preferred because of their size and availability. The smaller size of the mouse decreases the volume of fluids which must be handled in performing the requisite analysis of the immune response.

The animal model may be rendered immunodeficient by any available means which permits the animal to accept the donor organ and react to the organ graft in a manner which permits its use as a model for human allograft rejection. Basically, all or substantially all of the animal's immune response is inactive or destroyed. This immunodeficiency may be effected by using a natural or recombinant agent as well as via chemical agents. It is believed that any means of inactivating or depleting enzymes, such as RAG1 and RAG2, which are crucial to the animal's immune system, can be used to effect immunodeficiency. Viral agents or genetic mutations which are known to generate immunodeficient mice, e.g. SCID, can be employed. Since the SCID mice are commercially available, it is the most preferred immunodeficient animal for use in the model.

One key aspect of the novel model is that the animal contains microvessels lined with human endothelial cells. These cells express a critical combination of surface proteins that are not found on mouse endothelial cells or other human cell types. These cells are present in the microvessels of vascularized organs (i.e. which is referred to in the skin as the superficial vascular plexus of the dermis). Illustrative of sample organs include skin, lung, kidney and heart. Often, an excellent source of the endothelial cells is an intact dermal superficial vascular plexus of the skin. The intact dermal superficial vascular plexus is preserved within a partial split thickness human skin section, and preferably, the source is adult of about age fifteen or above. The endothelial cells may also be genetically or pharmacologically altered to increase or decrease their interaction with the T lymphocytes. The term genetically altered refers to any recombinant method of modifying the endothelial cell. One example is to add a foreign gene to the endothelial cells to provide a desired characteristic or to provide a marker. On the other hand, pharmacologically altered refers to the addition of biologically active chemical compound to the endothelial cells or to their environment within the vascular plexus.

The amount of endothelial cells employed is such that when exposed to the circulating blood of the animal model the human T lymphocytes contained in the blood and endothelial cells interact to generate an inflammatory immune response. If the source of endothelial cells is the donor organ, no additional endothelial cells are needed. Otherwise, preferably, one should use at least about 100,000 endothelial cells.

In alternative embodiments, it is noted that one may be able to use substitute "synthetic microvessels". These can be prepared in vitro from endothelial cells of the donor of the organ by inducing cultured cells to form tubular structures or introducing them within the gel of an extracellular matrix component, e.g. collagen. In the case of synthetic microvessels, a substitute structure can be employed instead of the actual organ. This substitute structure is selected to permit the interaction of the endothelial cells and the T lymphocytes.

The source of the organ is a mammal differing from the immunodeficient animal. Although preferably, a human organ is employed in the model of this invention, organs from non-human can be used to evaluate their potential as a source of acceptable transplants to humans.

The animal model employs human T lymphocytes from the spleen, lymph nodes or blood. One can employ human T lymphocytes or human lymphocytes from which the T lymphocytes (T cells) have not been separated. The latter is convenient source since it avoids additional separation steps. The lymphocytes can be obtained from an in vitro culture or an enriched or a depleted lymphocyte subpopulation. For example, the human lymphocyte population may be treated with antibodies to deplete Natural Killer cells, $CD8^+$, $CD4^+$, etc. The lymphocytes are allogeneic to the donor of the graft unless one is conducting an autologous study.

The T cells may also be genetically or pharmacologically altered to increase or decrease their interaction with the endothelial cells.

The human T lymphocytes are present in an effective amount; wherein said effective amount is the number of T lymphocytes which are sufficient for the animal to exhibit responses of human allograft rejection. The range of useful amounts is easily obtained by conducting preliminary experiments to ascertain these values. For mice, the amount of human peripheral blood mononuclear leukocytes may vary from about $1\times10^7$ to about $1\times10^9$ cells. Preferably, the amount of human mononuclear leukocytes is about $1\times10^8$ to about $1\times10^9$ cells, with the amount of choice being about $3\times10^8$. Since the peripheral blood mononuclear leukocytes contain B lymphocytes, T lymphocytes and Natural Killer cells, the amounts to be used for other sources of T lymphocytes will vary depending on the purity or concentration of T lymphocytes contained therein. For other sources, the above ranges of purified T lymphocytes or cloned T lymphocytes should be decreased by about 10 to about 90 percent, preferably about 25% to about 50 percent, in accordance with whether a pure or substantially pure T lymphocyte population or lymphocyte population is used.

In addition, the animal model should contain at least one agent (referred to as an NK depletion agent) capable of rendering inactive the Natural Killer cells of the animal model unless this part of the animal's immune system has been rendered inactive by the agent causing the immunodeficiency. Any material, chemical, recombinant protein or microorganism capable of acting as an NK depletion agent can be used; however, any material selected must not interfere with the ability of the model to exhibit the desired human immune response. Preferably, the depletion agent is an antibody selectively reactive with Natural Killer cells of the animal model. For mice, preferably, a mouse NK depletion agent is an antibody to asialo GM1.

It is further noted that one can also employ genetic strains of rodents or mice which have sufficiently decreased activity of the NK cells such that the desired human immune response is unaffected.

The NK depletion agent is present in an amount sufficient to substantially deplete the animal's active Natural Killer cells. The amount may vary dependent on the animal and type of depletion agent selected. The range of useful amounts is easily obtained by conducting preliminary experiments to ascertain these values. For mice, the amount of anti-asialo GM1 antibody used as a depletion agent may vary from about 10uL to about 100uL administered intravenously. Preferably, the amount of anti-asialo GM1 antibody is about 25uL to about 50uL, with the amount of choice being about 50uL.

Another embodiment of this invention relates to a method of preparing an immunodeficient animal for studying human allograft rejection. The method comprises:

(a) grafting a portion of human skin to said immunodeficient animal, said graft containing microvessels lined with human endothelial cells;

(b) delivering at least one agent capable of rendering inactive the Natural Killer cells of the non-primate animal; said agent being delivered in an amount sufficient to substantially deplete the animal's active Natural Killer cells; and (c) subsequent to completing the skin graft in step (a), delivering to the animal an effective amount of human T lymphocytes allogenic to the donor for the skin graft.

In preferred embodiments of this invention, an NK depletion agent is added once the organ graft has at least partially healed. In the most preferred embodiments, the NK depletion agent is added after the graft has substantially healed. The graft is healed upon (1) the inosculation of the microvessels of the donor organ and those of the rodent animal model and (2) the subsidence of inflammation in the graft bed associated with the surgical implantation (as opposed to the inflammatory immune response occurring after the T lymphocytes are added). It is noted that the healing time may vary with the selection of the organ, graft procedure and choice of animal model. However, optimization of these variables is readily obtained by conventional experimental procedures.

In the preferred embodiments of the skin graft model, the NK depletion agent is added at least about 5 days after completing the vascular skin graft. More preferably, the NK depletion agent is added at least about 10 days after completing the vascular skin graft.

Although the human T lymphocytes can be added about 10 days after completing the vascular skin graft, in the preferred embodiments, the human T lymphocytes are added after the graft has substantially healed. In alternatively preferred embodiments, the human T lymphocytes are added at the time of adding the NK depletion agent or thereafter. It was also discovered that the addition of the human T lymphocytes after the NK depletion agent can further enhance the ability of the animal model to exhibit the desired response. Therein, in more preferred embodiments, the human T lymphocytes are added at least about 8 hours after the NK depletion agent, and more preferably, the human T lymphocytes are added at least about 20 hours after the NK depletion agent, but in most instances within about 60 hours after the NK depletion agent.

It is apparent that the animal model of this invention can be used to evaluate potential therapeutic reagents to inhibit human T cell-mediated injury which accompany human organ allografts. The model and methods of this invention can be used to discover potential reagents and the range of amounts which are effective for inhibition. The amount of reagent may vary with each unique reagent; however, sufficient amounts can be readily determined by preliminary experiments, such as comparison experiments using effective amounts of reagents capable of preventing the T cell mediated destruction of the microvessels. The presence or absence of the T cell mediated response and microvessel destruction can be observed and quantitated by techniques used herein or other known techniques.

The following examples illustrate several embodiments of the present invention but they should not be construed to limit the scope of the present invention.

EXAMPLES

The described experiments are conducted on numerous mice, including controls. The experimental methods and corresponding results are summarized by the following representative examples.

Materials and Methods

Animals

C.B-17 SCID mice purchased from Harlan Sprague-Dawley are used at ages 5 to 8 weeks. The animals are housed in micro-isolator cages in a pathogen free environment and fed sterilized water and mouse chow.

Antibodies

Rabbit anti-asialo $GM_1$ antibodies for mouse NK cell depletion are available from Wako Chemicals (Richmond, Va.). The following antibodies are used for immunohistochemistry: mouse anti-human T cell (anti-CD3), mouse anti-human monocyte (anti-CD68), mouse anti-human Langerhans cell (anti-CD1a), mouse anti-human platelet-endothelial cell adhesion molecule (anti-CD31; from Dako, Carpenteria, Calif.), and hamster anti-mouse CD31 (from Steve Bogan, Boston University, Boston, Mass.). Mouse anti-human intercellular adhesion molecule-1 (anti-ICAM-1, RR 1/1; from T. Springer, Institute for Blood Research, Harvard University, Boston, Mass.), mouse anti-human HLA-DR (LB3.1, from J. Strominger, Harvard University, Cambridge, Mass.), mouse anti-human CD4 and mouse anti-human CD8 (from Becton Dickinson, Mountain View, Calif.), mouse anti-human vascular cell adhesion molecule-1 (anti-VCAM-1, E1/6; from Dr. M. P. Bevilacqua, Amgen, San Diego, Calif.), and mouse anti-human E-selectin (H4/18, see publication (24)); rat anti-human perforin (purchased from T Cell Diagnostics, Cambridge, Mass.); rat anti-mouse macrophage (F4/80; from Biosource, Camarillo, Calif.); hamster anti-mouse CD3, and rat anti-mouse CD1a (from Pharmingen, San Diego, Calif.). The following antibodies are used for direct immunofluorescence and flow cytometry: fluorescein isothiocyanate (FITC)-conjugated mouse anti-human CD3, FITC-conjugated mouse anti-human CD4, and phycoerythrin (PE)-conjugated mouse anti-human CD8 (from Exalpha, Cambridge, Mass.); red 613-conjugated rat anti-mouse CD45 (from Gibco/BRL,Grand Island, N.Y.).

Peripheral blood mononuclear cell isolation and engraftment

Peripheral blood mononuclear cells (PBMC) are isolated from adult volunteer donors by leukophoresis and purified on lymphocyte separation medium (Organon Teknika Corp., Durham, N.C.) according to the instructions of the manufacturer. Perform 2 washes in RPMI 1640 culture medium (Gibco, Grand Island, N.Y.) and then inject $3 \times 10^8$ cells intraperitoneally into each mouse.

Preliminary experiments are conducted to determine the optimal number of PBMC, using concentrations ranging between $3 \times 10^6$ to $6 \times 10^8$. Effectiveness is assessed by optimizing the circulating levels of human T cells and the rejection of the engrafted skin.

Human Immunoglobulin and circulating lymphocyte determination

Human immunoglobulin-G (IgG) concentrations and circulating human lymphocyte frequency are determined from heparinized blood collected by retro-orbital venipuncture. A sandwich ELISA is used to quantitate human IgG levels (25). The ELISA is developed using o-phenylenediamine (Sigma) as the enzyme substrate and absorbance at 530 nm is measured on a MR7000 microplate reader (Dynatech, Chantilly, Va.). Serum levels of human IgG are quantified by comparison with purified human IgG (Cappel, Durham, N.C.); the sensitivity of the assay is 10 ng/mL. Assays for murine immunoglobulin are performed in a similar fashion using purified sheep anti-mouse IgG as the capture reagent, and peroxidase-conjugated sheep anti-mouse IgG as the second antibody (both purchased from Cappel). Mice with murine IgG levels greater than 1ug/mL are excluded from the studies. The frequency of circulating human T lymphocytes as a proportion of blood leukocytes is determined by direct immunofluorescence using a FACSort (Becton Dickinson). An aliquot of heparinized blood is treated with red cell lysis buffer (0.3M $NH_4Cl$, 0.2 M $KHCO_3$, 0.8 mM EDTA in distilled water) and washed with ice cold PBS/ 2%BSA. The cells are stained as described previously.

Skin engraftment

The outermost portions of normal adult human breast skin are harvested in approximately 500–700 μm thick sheets using a Goulian dermatome knife, gauge size 0.016 (Weck, GM, Branford, Conn.), and cut in approximately 7×7 mm pieces which were kept in RPMI 1640 at 4° C. until transplantation, usually within 1–2 hours of harvest. C.B-17/SCID mice are anesthetized by i.p. injection of Xylozine (3 mg/kg; Lloyd Laboratories, Shenandoah, Iowa) and Ketamine (3 mg/kg; Aveco, Fort Dodge, Iowa). The skin was shaved, and two 5×5 mm skin segments were excised from the back of each mouse, and the defects are immediately covered with the human skin grafts, and fixed with disposable skin staples (3M, St. Paul, Minn.). Grafts are individually harvested at the indicated times using the same anesthesia protocol.

Histology and immunohistology

Each skin sample is used to prepare 3 μm paraffin—embedded sections stained with hematoxylin and eosin, and 4 μm cryostat sections are used for immunohistochemical staining. The immunohistochemical staining protocol is described previously (26). In brief, the first mAb is visualized using the ABC peroxidase Vectastain kit (Vector) and stained in red by 3-amino-9-ethylcarbazole (Sigma Chemical Co., St. Louis, Mo.). For double staining, the second mAb is visualized using the alkaline phosphatase anti-alkaline phosphatase (APAAP) technique and stained in blue by the alkaline phosphatase substrate kit obtained from Vector. Controls are performed using species matched non-binding control mAbs instead of specific mAbs.

Data analysis

All skin specimens are evaluated by two independent observers. First the number of human CD3, CD4, CD8, CD1a, and CD68 positive cells are assessed. A specimen is considered to show infiltration if the number of positive cells within the skin were at least tenfold over that seen in the respective control specimen (i.e. human skin graft without reconstituted PBMC in the same experiment). Second, the presence of E-selectin, VCAM-1, ICAM-1 or HLA-DR expression is assessed separately for each cell type in each specimen and scored semiquantitatively (−=negative, +=discrete, ++=moderate, +++=strong). Tissue morphology and tissue damage due to allogeneic PBMC reconstitution are assessed in paraffin-embedded specimens.

Results

Engraftment of human PBMC to C.B-17 SCID mice

Figure 1:
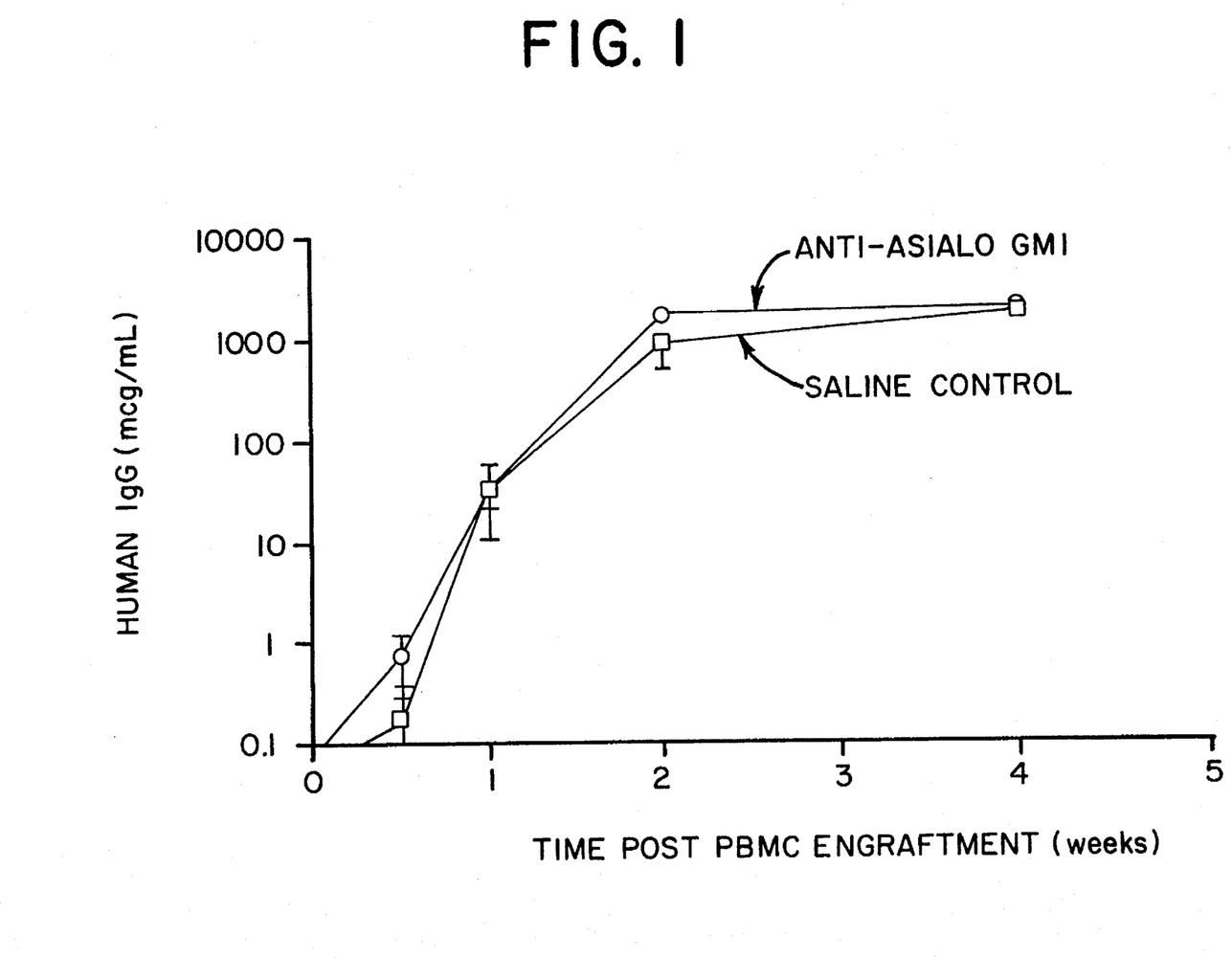
FIG. 1 illustrates the effect of murine Natural Killer (NK) cell depletion on human IgG concentrations after engraftment of human PMBC into SCID mice. The graph depicts experiments wherein C.B-17 SCID mice, pretreated with either saline (open symbols) or anti-asialo GM1 (closed symbols), received $3 \times 10^8$ human PBMC by intraperitoneal injection as described in the Methods section of the examples (human IgG concentrations in plasma are determined by ELISA).
Figure 2:
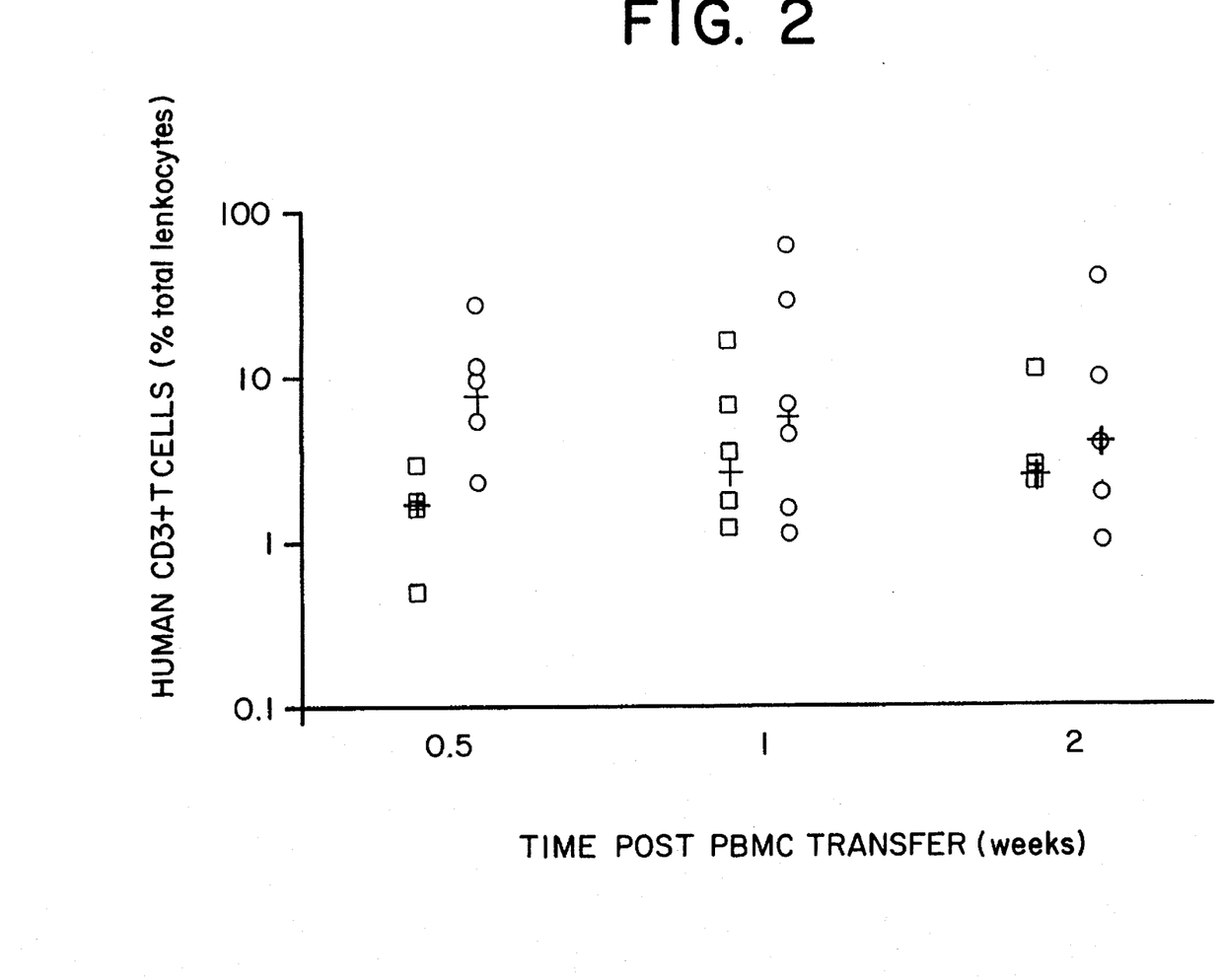
FIG. 2 illustrates the effect of murine Natural Killer (NK) cell depletion on circulating leukocytes after engraftment of human PMBC into SCID mice. The graph depicts experiments wherein C.B-17 SCID mice, pretreated with either saline (open symbols) or anti-asialo GM1 (closed symbols), received $3 \times 10^8$ human PBMC by intraperitoneal injection as described in the Methods section of the examples. The fraction of total peripheral blood leukocytes (human $CD3^+$ +murine $CD45^+$) staining for human CD3 was determined by direct immunofluorescence and flow cytometry. Data points represent individual mice, and the group mean is displayed as closed symbol.

Human PBMC are successfully engrafted (i.e. as noted by observance of the persistence of circulating T cells in the graft for up to 1–2 months) into C.B-17 SCID mice. Successful engraftment is determined by serum human IgG concentrations of approximately 1000 μg/mL at day 14, and detectable levels of circulating human T cells of up to 60% of circulating leukocytes. Preliminary experiments establish the optimum number of PBMC to be transferred as $3 \times 10^8$ cells and that depletion of mouse NK cells using a polyclonal antibody to asialo-GM1 increases the frequency of circulating human T cells at days 7–14 without increasing human IgG concentrations. Representative values are presented in FIGS. 1 and 2.

Histology of human skin graft on C.B-17/SCID mice

Partial thickness human skin grafts are routinely accepted by C.B-17 SCID mice without macroscopic or microscopic signs of necrosis, which is determined by histological examination. To optimize engraftment, the dermis is shaved as thin as possible while still maintaining the human dermal superficial vascular plexus. Specimens from 500–700 μm appear optimal. Seven days after engraftment, granulation tissue is evident at the base of the graft. Mouse and human capillaries (defined by double staining with anti-human CD31 and anti-mouse CD31 mAbs) appear to intermingle, with focal evidence of microvessel anastomosis at the graft margins. Human CD31$^+$ vessels persist within the human dermis and contain intraluminal erythrocytes indicating perfusion with mouse blood. The graft contains a few human CD3$^+$/CD4$^+$ T cells and human CD68$^+$ macrophages scattered within the dermis at levels comparable to those seen in pre-graft specimens. CD1a$^+$ human Langerhans cells within the epidermis are also present at pre-graft levels. Human CD3$^+$/CD8$^+$T cells are virtually absent.

Fourteen days after engraftment, the granulation tissue at the base of the human graft is largely resolved. Graft microvessels lined by human CD31$^+$ endothelium appear to be well perfused. Occasional microvessels lined with mouse CD31$^+$ endothelium are also noted within the graft. The boundary between the human and mouse epidermis is sharply demarcated, and the human basal cell layer showed normal differentiation, except for focal areas with intercellular edema and rare single necrotic keratinocytes. The epidermal thickness is comparable to the pregraft specimen, and the rete peg pattern is well preserved. There was little evidence for immunological activation in the resting tissue. Human endothelium does not express E-selectin or VCAM-1 molecules. ICAM-1 and HLA-DR molecules were weakly expressed on the endothelium at levels comparable to pregraft specimens. Keratinocytes were HLA-DR negative and ICAM-1 expression are only detectable at very low levels on the basal keratinocytes.

Allogeneic lymphocyte response to skin grafts

The following optimal three step procedure is used to examine interactions between circulating human T cells and graft microvessels lined by human vascular endothelial cells. First, split thickness human skin is grafted onto C.B-17/SCID mice and allowed to heal for 14 days. Allowing the skin grafts to heal prior to the introduction of allogeneic human PBMC promotes perfusion of the skin graft through anastomosed human microvessels. Second, mouse NK cells are depleted with an intravenous injection of anti-asialo GM$_1$. Depletion of recipient mouse NK cells promotes engraftment of the human PBMC (21, 28). Third, 24 hours after NK cell depletion, human PBMCs, allogeneic to the skin donor, are introduced into the peritoneum. This above procedure produces a perivascular lymphocytic infiltrate in more than 90% of the animals examined 7 to 14 days after the injection of human PBMCs. Pretreatment of several mice by i.v. injection of 50 µl anti-asialo GM$_1$ antibody (Wako) 12–24 hours before PBMC engraftment and at the time of skin engraftment can lead to an inflammatory infiltrate at the base of the graft that prevents mouse-human microvessel inosculation. The above protocol enhances the probability that human T lymphocytes introduced into the peritoneal cavity of the mouse will circulate and contact the superficial vascular plexus of the human skin graft. It is noted that some of the circulating human T lymphocuytes specifically localize to allogeneic skin grafts in a perivascular distribution, but not to xenogeneic mouse skin.

Three experiments are performed, obtaining similar results. Skin grafts examined one day after PBMC reconstitution are indistinguishable from control specimens. By six days after PBMC reconstitution, 3/5 specimens show focally damaged vessels characterized by dilated lumens, fibrin thrombi, and extravasated red blood cells. Some EC, in close apposition to T cells, have condensed nuclei indicative of cell injury. Clusters of intraluminal human CD4$^+$ cells exhibit adherence to the endothelium and some (score: +) CD4$^+$ and CD8$^+$ T cells are found in a perivascular distribution. The numbers of human CD68$^+$ macrophages and CD1a$^+$ Langerhans cells are unchanged compared to controls. Most strikingly, in 5/5 specimens, VCAM-1 (score: ++) and HLA-DR (score: +++) expression is strongly upregulated on most of the human dermal vessels. At this time ICAM-1 expression remains unchanged from the control specimens and E-selectin expression is not induced, and most human keratinocytes strongly (score: +++) expressed HLA-DR, but ICAM-1 expression is not upregulated on these cells.

By 11 days after PBMC reconstitution the epidermis shows areas of marked acanthosis, although individual keratinocyte morphology is indistinguishable from day 1. Five of five specimens show infiltrates of human leukocytes. In 3/5 specimens, the infiltrate is moderate (score: ++) and in 2/5 discrete (score: +). The infiltrate is comprised of human CD3$^+$ T cells with approximately equal numbers of CD4$^+$ and CD8$^+$ cells, most expressing CD25, a marker of activation. Human blood vessels within the infiltrate are dilated, with fibrin thrombi and extravasated red blood cells noted. Perforin-positive T cells are found in close contact to damaged EC. Adjacent areas contain knots of EC, suggesting EC proliferation. CD68$^+$ macrophages and CD1a$^+$ Langerhans cells are unchanged compared to controls. VCAM-1 (score: +++) and HLA-DR (score: +++) expression on EC are more strongly expressed compared to vessels observed on day 6. Furthermore, ICAM-1 (score: ++) is now strongly upregulated on the vascular endothelium, but E-selectin is not detected. Keratinocyte HLA-DR is either equal or diminished compared to the 6 day specimens (score: ++ to +++), whereas ICAM-1 is now upregulated (score: ++) compared to earlier specimens.

By day 16 after PBMC reconstitution, the epidermis remains acanthotic and there is a focal epidermotropic T cell infiltrate and disorganization of the basal cell layer without keratinocyte necrosis. Fifteen of 16 specimens show strong (score: +++) CD3$^+$ T cell infiltrates, comprised of equal numbers of CD4$^+$ and CD8$^+$ cells. Intact human blood vessels can no longer be identified. In the residual human microvessels the vessel wall is disrupted, with extensive fibrin thrombi and extravasated red blood cells. Perforin-positive lymphocytes are again noted in close relationship to the residual EC. Many infiltrating T cells appear as blasts, and multiple mitotic figures are evident. There is an increase in perivascular CD68$^+$ macrophages, but CD1a$^+$ Langerhans cells are unchanged, compared to controls. Human CD31 staining differs from earlier specimens in that only few vascular structures are identified. Endothelial structures staining for VCAM-1, ICAM-1, or HLA-DR are also reduced and are not readily distinguished from staining of infiltrating leukocytes. Keratinocyte expression of HLA-DR and ICAM-1 varies widely between specimens (score: + to +++).

Observations from the Experiemnts
Activty of Alloantigen-specific Cytolytic T cells The human graft dermal superficial vascular plexus becomes activated, co-incident with the onset of T cell infiltration, as indicated by the expression of VCAM-1, and MHC class II molecules. A subset of the human CD3+ T cells differentiate to display a cytolytic phenotype marked by expression of the granule protein perforin, and by approximately two weeks following re-constitution with allogeneic human PBMC, the human superficial vascular plexus of the skin graft is destroyed, likely as a manifestation of the functional activity of alloantigen-specific cytolytic T cells.

Destruction of the Human Dermal Superficial Vascular Plexus

The interpretation from the above experiments that the destruction of the human dermal superficial vascular plexus is mediated by cytolytic T cells is supported by the following observations. First, there is evidence of destruction of the human dermal superficial vascular plexus only in mice reconstituted with allogeneic human lymphocytes. This observation indicates that the vascular damage is the result of neither effects of graft ischemia, nor of a xenogeneic immune response mediated by mouse NK cells or other leukocytes. Second, a human T cell infiltrate precedes the loss of the human endothelium in a temporal profile consistent with the activation and differentiation of T cells in the allogeneic setting. Activation of the dermal T cells is inferred from the expression of the high affinity IL-2 receptor, CD25, a marker of T cell activation, and by the demonstration of the presence of cytolytic granules. Furthermore the functional effects of cytokines produced by activated T cells are evident by the induction of MHC class II and VCAM-1 on the vascular endothelium, and by the induction of ICAM-1, and MHC class II molecules on the keratinocytes in the epidermis. Finally, T cell blasts with numerous mitotic figures are seen in the skin harvested at day 16, presumably proliferating in response to alloantigen stimulation. In a preliminary experiment, T cells recovered from an infiltrated skin graft proliferated in vitro in response to dermal microvascular endothelial cells cultured from the skin graft donor, but not from a third party donor.

The Role of EC Adhesion Molecules in Allograft Rejection

ICAM-1 is constitutively expressed on the microvessel endothelial cells, and neither VCAM-1 nor E-selectin are present. As the immune response to the graft evolves, however, VCAM-1 is upregulated early (by day 6) in contrast to E selectin which is not modulated. ICAM-1 expression on the endothelium is induced later in the response. These observations suggest that VCAM-1 may be a relevant adhesion molecule to recruit T cells to sites of inflammation in the skin. Previous work in other systems has suggested the role of E-selectin as a dermal addressin (29); however, from the above experiments, arguably, the expression of E-selectin by the dermal superficial vascular plexus is not required for lymphocyte infiltration.

Absence of Necrosis of the Skin Graft

Frank necrosis of the skin graft is not observed. One reason for this observation may be that in this model, unlike traditional allogeneic skin allograft models, the graft enjoys a dual blood supply, derived from both the anastomosis of the remnant human microvascular arcades with mouse capillaries, and from the ingrowth of new mouse vessels. As the human immune response develops, selective destruction of the human vascular elements ensues, but the epidermis remains viable, presumably nourished by the remaining mouse capillaries. Necrotic keratinocytes are observed only rarely.

PUBLICATIONS CITED:

Publications cited in the above examples are incorporated herein by reference.

1. Dvorak, H. F., Mihm, M. C., Dvorak, A. M., Barnes, B. A., Manseau, E. J. & Galli, S. J. (1979) J. Exp. Med. 150, 322–337.
2. Dvorak, H. F., Mihm, M. C., Dvorak, A. M., Barnes, B. A. & Galli, S. J. (1980) J. Invest. Dermatol . 74, 240–248.
3. Leszczynski, D., Lasczynska, M., Halttunen & Häyry, P. (1987) Kidney Int. 31, 1311–1316.
4. Bishop, G. A., Waugh, J. A., Landers, D. V., Krensky, A. M. & Hall, B. M. (1989) Transplantation 48, 408–414.
5. Matsumoto, Y., McCaughan, G. W., Painter, D. M. & Bishop, G. A. (1993) Transplantation 56, 69–75.
6. Rosenberg, A. & Singer, A. (1992) Annu. Rev. Immunol . 1992, 333–358.
7. Mosier, D. E., Gulizia, R. J., Baird, S. & Wilson, D. B. (1988) Nature 335, 256–259.
8. Dorschkind, K., Keller, G. M., Phillips, R. A., Miller, R. G., Bosma, G. C., O'Toole, M. & Bosma, M. J. (1984) J. Immunol. 132, 1804–1808.
9. Schuler, W., Weiler, I. J., Schuler, A., Phillips, R. A., Rosenberg, N., Mak, T. W., Kearney, J. F., Perry, R. P. & Bosma, M. J. (1986) Cell 46, 963–972.
10. Fulop, G. M. &Phillips, R. A. (1990) Nature 347, 479–482.
11. Carlsson, R., Martensson, C., Kalliomaki, S., Ohlin, M. & Borrebaeck, C. A. (1992) J. Immunol. 148, 1065–1071.
12. Duchosal, M. A., Eming, S. A., Fischer, P., Leturcq, D., Barbas, C. 3., McConahey, P. J., Caothien, R. H., Thornton, G. B., Dixon, F. J. & Burton, D. R. (1992) Nature 355, 258–262.
13. Leader, K. A., Macht, L. M., Steers, F., Kumpel, B. M. & Elson, C. J. (1992) Immunology 76, 229–234.
14. Markham, R. B. & Donnenberg, A.D. (1992) Infection & Immunity 60, 2305–2308.
15. Cavacini, L. A., Kennel, M., Lally, E. V., Posner, M. R. & Quinn, A. (1992) Clin. Exp. Immunol. 90, 135–140.
16. Furukawa, T., Watanabe, M., Kubota, T., Yamaguchi, H., Teramoto, T., Ishibiki, K. & Kitajima, M. (1992) Jpn. J. Cancer Res. 83, 894–898.
17. Hesselton, R. M., Koup, R. A., Cromwell, M. A., Graham, B. S., Johns, M. & Sullivan, J. L. (1993) J. I. D. 168, 630–640.
18. Nonoyama, S., Smith, F. O. & Ochs, H. D. (1993) J. Immunol. 151, 3894–3901.
19. London, N. J., Thirdborough, S. M., Swift, S. M., Bell, P. R. & James, R. F. (1991) Transplant. Proc. 23, 749.
20. Kawamura, T., Niguma, T., Fechner, J. J., Wolber, R., Beeskau, M. A., Hullett, D. A., Sollinger, H. W. & Burlingham, W. J. (1992) Transplantation 53, 659–665.
21. Murphy, W. J., Conlon, K. C., Sayers, T. J., Wiltrout, R. H., Back, T. C., Ortaldo, J. R. & Longo, D. L. (1993) J. Immunol. 150, 3634–3642.
22. Rendt, K. E., Barry, T. S., Jones, D. M., Richter, C. B., McCachren, S. S. & Haynes, B. F. (1993) J. Immunol. 151, 7324–7336.
23. Tary-Lehmann, M. & Saxon, A. (1992) J. Exp. Med. 175, 503–516.
24. Pober, J. S., Bevilacqua, M. P., Mendrick, D. L., Lapierre, L. A., Fiers, W. & Gimbrone, M. A. (1986) J. Immunol. 136, 1680–1687.
25. Macy, E. , Kemeny, M. & Saxon, A. (1988) FASEB J. 2, 3003–3009.
26. Petzelbauer, P., Bender, J. R., Wilson, J. & Pober, J. S. (1993) J. Immunol. 151, 5062–5071.
27. Yan, H.-c. , Juhasz, I., Pilewski, J. , Murphy, G., Herlyn, M. & Albelda, S. M. (1993) J. Clin. Invest. 91, 986–996.
28. Murphy, W. J., Bennett, M., Anver, M. J., Baseler, M. & Longo, D. (1992) Eur. J. Immunol. 22, 1421–1427.
29. Picker, L. J., Kishimota, T. K., Smith, C. W., Warnock, R. A. & Butcher, E. C. (1991) Nature 349, 796–799.

We claim:

1. An immunodeficient rodent animal, wherein the immunodeficient animal comprises:

(i) a graft of a vascularized organ tissue of a mammal, wherein said organ is selected from the group consisting of skin, kidney, bronchus, and heart, said organ containing microvessels lined by endothelial cells from the donor of the organ and said microvessels being inosculated with microvessels of said immunodeficient animal;

(ii) circulating human T lymphocytes allogeneic for said graft in an amount sufficient for said animal to exhibit an acute T-cell mediated immune response directed against said graft; and (iii) at least one agent capable of rendering inactive the Natural Killer cells of the animal rodent, said agent being present in an amount sufficient to substantially deplete the animal's active Natural Killer cells.

2. The animal of claim 1 wherein said animal is a mouse.

3. The animal of claim 1 wherein the organ is from a human.

4. The animal of claim 1 wherein the organ is from a non-human mammal other than a rodent.

5. The animal of claim 1 wherein human peripheral blood mononuclear leukocytes are the source of human T lymphocytes.

6. The animal of claim 1 wherein the NK depletion agent is an antibody raised against Natural Killer cells of the animal.

7. The animal of claim 1 wherein the NK depletion agent is an antibody to asialo GM1.

8. The animal of claim 1 wherein the microvessels are synthetic.

9. The animal of claim 1 wherein the human T lymphocytes are obtained from one or more of spleen, lymph nodes or blood.

10. The animal of claim 1 wherein the human T lymphocytes are obtained from an in vitro culture or an enriched or a depleted lymphocyte subpopulation.

11. The animal of claim 1 wherein the human T lymphocytes are provided at least 5 days after the organ graft.

12. The animal of claim 11 wherein a depletion agent for Natural Killer cells of the rodent is added in conjunction with the human T lymphocytes.

13. The rodent of claim 3 wherein said human skin graft is grafted having a substantially intact dermal superficial vascular plexus.

14. The animal of claim 2 wherein the rodent is a SCID mouse.

15. The animal of claim 14 wherein the organ tissue is from a human.

16. The animal of claim 15 wherein the NK depletion agent is an antibody raised against Natural Killer cells of the animal.

17. The rodent of claim 1 wherein the organ graft is human skin.

18. A method of preparing an immunodeficient rodent animal for studying human T cell mediated immune response comprising:

(a) grafting a portion of an organ from a mammal to an immunodeficient rodent animal, said graft containing microvessels lined by endothelial cells from the donor of the organ; said organ selected from the group consisting of skin, kidney, bronchus and heart;

(b) allowing said graft to heal, wherein said healing comprises inosculation of the microvessels of said graft and microvessels of said immunodeficient animal;

(c) subsequent to said healing, delivering to the animal human T lymphocytes allogeneic for said graft in an amount sufficient for said animal to exhibit an acute T-cell mediated immune response directed against said graft; and (d) delivering at least one agent capable of rendering inactive the Natural Killer cells of the rodent animal; said agent being delivered in an amount sufficient to substantially deplete the rodent's active Natural Killer cells.

19. The method of claim 18, wherein the NK depletion agent is added at least 5 days after completing the organ graft.

20. The method of claim 18, wherein the NK depletion agent is added at least 10 days after completing the organ graft.

21. The method of claim 18 wherein the NK depletion agent is added after the organ graft has substantially healed.

22. The method of claim 18 wherein the human T lymphocytes are added after the NK depletion agent.

23. The method of claim 19, wherein the human T lymphocytes are added at least 12 hours after the NK depletion agent.

24. The method of claim 19, wherein the human T lymphocytes are added at least 12 hours after the NK depletion agent but within 48 hours.

25. The method of claim 24 wherein the human T lymphocytes are added at least 24 hours after the NK depletion agent.

26. A method of evaluating a reagent for its ability to inhibit an acute T cell mediated response in a human comprising:

(a) providing a reagent to the immune system of the rodent model of claim 1; and (b) determining the presence or absence of an acute T cell mediated response.

27. The method of claim 20 wherein the reagent is provided locally at the site of the organ graft.

28. The method of claim 26 wherein the reagent is provided to the blood supply of the animal.

29. The method of claim 26 wherein the immune response is the reaction of a human to an allograft.

30. A method of preparing an immunodeficient mouse for studying human T-cell mediated allograft rejection, said method comprising:

(a) grafting a portion of human skin to said immunodeficient mouse, said graft containing microvessels lined by human endothelial cells from said human skin and said graft microvessels becoming inosculated with microvessels of said immunodeficient mouse;

(b) delivering at least one agent capable of rendering inactive the Natural Killer cells of the mouse; said agent being delivered in an amount sufficient to substantially deplete the mouses' active Natural Killer cells; and (c) subsequent to completing the skin graft in step (a), delivering to the mouse an amount of human T lymphocytes allogeneic to the donor for the organ graft in an amount sufficient for said mouse to exhibit an acute T-cell mediated immune response directed against said graft.

31. An SCID mouse comprising:

(i) a graft of split thickness adult human skin, wherein said graft contains microvessels lined by human endothelial cells and said microvessels are inosculated with microvessels of said immunodeficient animal;

(ii) circulating human T lymphocytes allogeneic for said graft in an amount sufficient for said SCID mouse to exhibit an acute T-cell mediated immune response directed against said graft, wherein active Natural Killer cells in said mouse are substantially depleted.

32. A method of preparing an SCID mouse for studying human T-cell mediated immune responses, said method comprising:

(a) grafting split thickness adult human skin to said mouse, wherein said graft contains microvessels lined by human endothelial cells;

(b) allowing said graft to heal, wherein said healing comprises inosculation of the microvessels of said graft and microvessels of said immunodeficient animal; and (c) subsequent to said healing; delivering to said animal human peripheral blood mononuclear leukocytes allogeneic for said graft in an amount sufficient for said animal to exhibit an acute T-cell mediated immune response directed against said graft, wherein active Natural Killer cells in said mouse are substantially depleted.

33. A method as defined in claim 32 wherein the amount of human peripheral blood mononuclear leukocytes delivered to said mouse is between about $1 \times 10^8$ and $1 \times 10^9$ cells/mouse.

34. A method as defined in claim 32 wherein said human T lymphocytes are delivered to said mouse by intraperitoneal administration.

* * * * *